US 6,656,129 B2

(12) United States Patent
Niles et al.

(10) Patent No.: US 6,656,129 B2
(45) Date of Patent: Dec. 2, 2003

(54) FLOW BASED INCENTIVE SPIROMETER (75) Inventors: Rex A. Niles, Oneida, NY (US);
Stephen D. Diehl, 1509 Brothertown Rd., Waterville, NY (US) 13480;
Patrick W. Olin, 3970 Peterboro Rd., Vernon Center, NY (US) 13477;
Deborah A. Laun, 4003 Bussey Rd., Syracuse, NY (US) 13215; David T. Middleton, Jr., Skaneateles, NY (US)

(73) Assignees: Stephen D. Diehl; Patrick W. Olin; Deborah A. Laun; David T. Middleton

( * ) Notice: Subject to any disclaimer, the term of this patent is extended or adjusted under 35 U.S.C. 154(b) by 0 days.

(21) Appl. No.: 09/764,636

(22) Filed: Jan. 18, 2001

(65) Prior Publication Data
US 2002/0151813 A1 Oct. 17, 2002

(51) Int. Cl.⁷ ................................. A61B 5/08
(52) U.S. Cl. ............... 600/540; 600/532; 600/538; 600/541
(58) Field of Search ................ 600/540, 538, 600/541, 539, 543, 532

(56) References Cited

U.S. PATENT DOCUMENTS

| 4,158,360 A | * | 6/1979 | Adams .................. 482/13 |
| 4,171,804 A | * | 10/1979 | Thead, Jr. ............... 482/13 |
| 4,232,683 A | | 11/1980 | Bartholomew et al. |
| 4,324,260 A | * | 4/1982 | Puderbaugh ............ 600/541 |
| 4,327,740 A | * | 5/1982 | Shuman ................. 600/541 |
| 4,363,328 A | * | 12/1982 | Poirier et al. ........... 600/541 |
| 4,391,283 A | | 7/1983 | Sharpless et al. |
| 4,425,923 A | * | 1/1984 | Gordon et al. .......... 600/540 |
| 4,444,202 A | | 4/1984 | Rubin et al. |
| 4,499,905 A | * | 2/1985 | Greenberg et al. ...... 482/13 |
| 4,944,306 A | * | 7/1990 | Alvino .................. 600/538 |
| 5,431,154 A | * | 7/1995 | Seigel et al. ......... 128/200.14 |
| 5,522,380 A | | 6/1996 | Dwork |
| 5,984,873 A | * | 11/1999 | Crumb et al. ........... 482/13 |
| 6,191,497 B1 | * | 2/2001 | Wickstead et al. ...... 307/11 |
| 6,238,353 B1 | * | 5/2001 | Weinstein et al. ...... 600/538 |

FOREIGN PATENT DOCUMENTS

WO          WO-9836687 A1  *  8/1998

* cited by examiner

Primary Examiner—Weilun Lo
Assistant Examiner—Darwin P. Erezo
(74) Attorney, Agent, or Firm—August E. Roehrig, Jr.; Hancock & Estabrook, LLP (57) ABSTRACT An improved flow based incentive spirometer operable through a range of user set flow rates and being adapted to receive a supplemental flow of Oxygen without requiring any change in the calibration of the device or effecting the patient's monitoring of usage. In this manner the spirometer may be utilized by a range of patients having quite distinct therapy needs. The device also features an integral information display receptacle in the base for storage of operational instructions. A portion of the base is transparent to that the information contained in the storage receptacle can be viewed by a patient while the device is in use, thereby permitting a patient to observe such things as the instructions for proper use of the incentive spirometer while using the device.

15 Claims, 10 Drawing Sheets

FLOW BASED INCENTIVE SPIROMETER

BACKGROUND OF THE INVENTION

1. Field of the Invention

This invention relates in general to respiratory therapy devices and, in particular, to a flow based incentive spirometer to encourage deep breathing exercise for the post-surgical prevention and treatment of atelectasis.

More specifically, but without restriction to the particular embodiment and/or use which is shown and described herein for purposes of illustration, this invention relates to a flow based incentive spirometer which will provide feedback to patients performing sustained maximal inspiration exercises, and is capable of being used by a patient with a supplemental source of Oxygen.

2. Description of Related Art

The use of flow based incentive spirometers for respiratory care and treatment is well known, but the instant spirometer provides specific advantages by addressing appropriate flow ranges through a cost effective, simple design having a number of different flow rate settings, accurate clinical feedback and repeatability, oxygen supplementation capability and ease of use. The present flow based spirometer includes a provision for supplemental oxygen to be provided to a user without interfering with the use of the spirometer throughout a range of flow rates.

SUMMARY OF THE INVENTION

It is an object of this invention to improve flow based incentive spirometers.

Another object of this invention is to provide a range of operational flow rates for use by a patient to ensure that an optimum flow rate is being utilized.

A further object of this invention is to provide a supply of oxygen to the inlet air of a flow based incentive spirometer without the oxygen which is being supplied interfering with the operation or calibration of the spirometer.

These and other objects are attained in accordance with the present invention wherein there is provided an improved flow based incentive spirometer operable through a range of user set flow rates and being adapted to receive a supplemental flow of Oxygen without requiring any change in the calibration of the device or effecting the patient's monitoring of usage. In this manner the spirometer may be utilized by a range of patients having quite distinct therapy needs.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

These and additional embodiments of the invention may now be better understood by referring to the following detailed description of the invention wherein the illustrated embodiment is described.

DETAILED DESCRIPTION OF THE INVENTION

Throughout this description, the preferred embodiment and examples shown should be considered as exemplars, rather than limitations on the apparatus and methods of the present invention.

Referring now to the drawings, there is shown a flow based incentive spirometer 100, having a handle portion 20, a base portion 30, a flow rate determining portion 50, and a monitoring portion 80. The handle portion 20 provides a convenient manner for holding and carrying the device, and for attaching the device to a bed, for example, where it can be readily accessible. The base portion 30 provides a platform upon which the device rests, and an integral information display receptacle for containing information such as the written instructions for use of the device which can be conveniently observed by a patient from the top or the bottom of the device when the device is in use. The flow rate determining portion 50 provides a user-selectable range of operative flow rates through which a patient can inhale inspiratory air to obtain the benefits of this therapy and a place for storing a mouthpiece which is used by a patient in withdrawing inspiratory air. The monitoring portion 80 provides a visual display for a patient to monitor the flow rate of inspiratory air during therapy.

The Flow Rate Determining Portion 50

As best illustrated in FIGS. 1, 2, 3 and 8, the flow rate determining portion 50 includes an inspiratory air withdrawal port 51 formed as an opening in a front wall 53 of the flow rate determining portion 50 through which a patient draws inspiratory air by means of a mouthpiece 91 connected to a flexible Popple tube 93. The tube 93 is sized to be securely positioned over the connecting port 51 in which may be carried a one-way valve, such as a spider supported flapper valve, to permit a patient to draw inspiratory air through the mouthpiece 91, but which blocks the passage of expiratory air from passing back into the device. To facilitate convenient access and storage of the mouthpiece 90, a storage slot is formed by a lipped recess or undercut 58 in the front wall 53 and an outwardly extending offset portion 59 formed in a back wall 54 to receive and retain the mouthpiece 90 therein.

Figure 5:
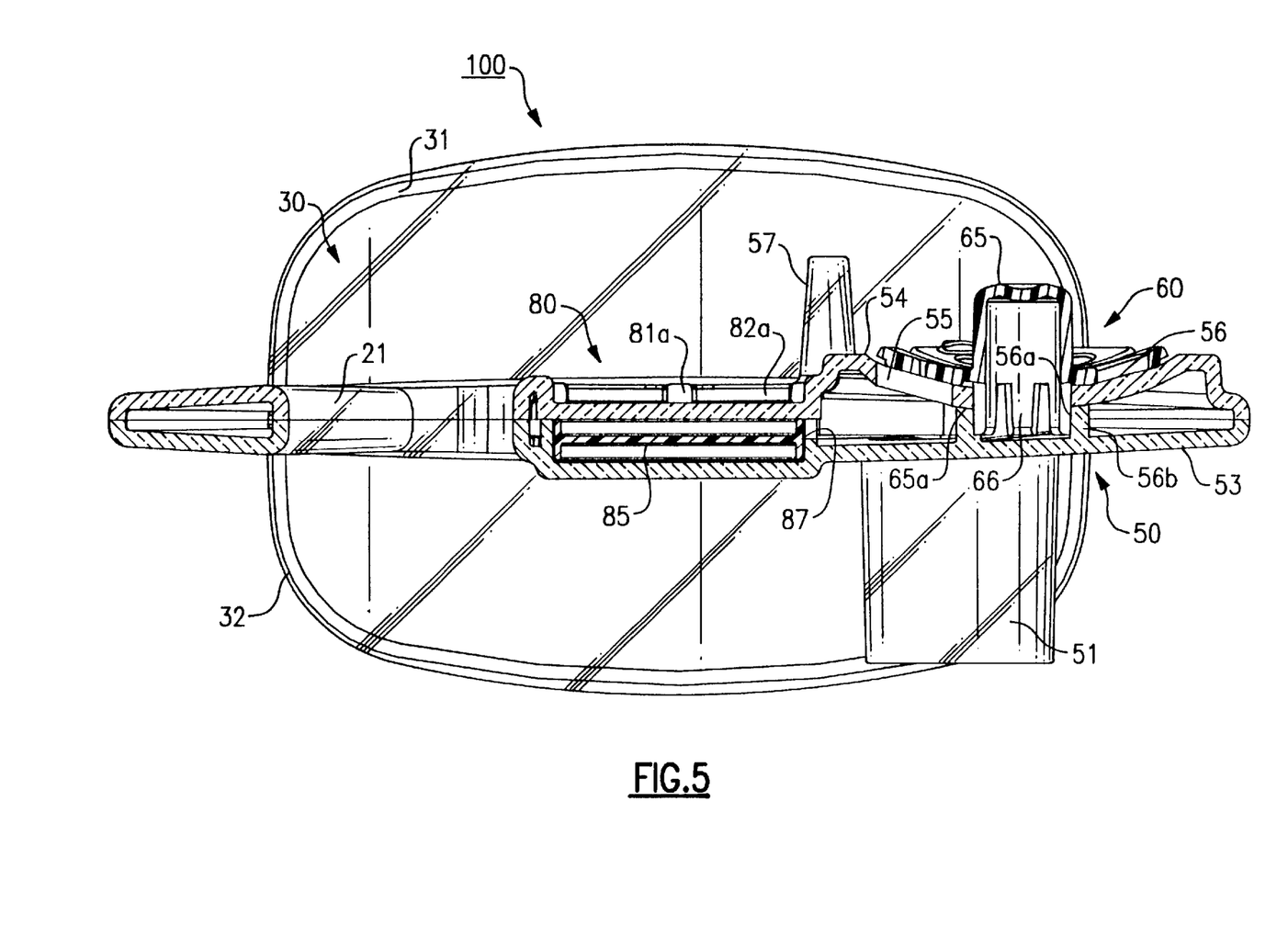
FIG. 5 is a cross-sectional view of the invention illustrated in FIG. 3 taken along line 5—5 to better illustrate the internal construction thereof.
Figure 6:
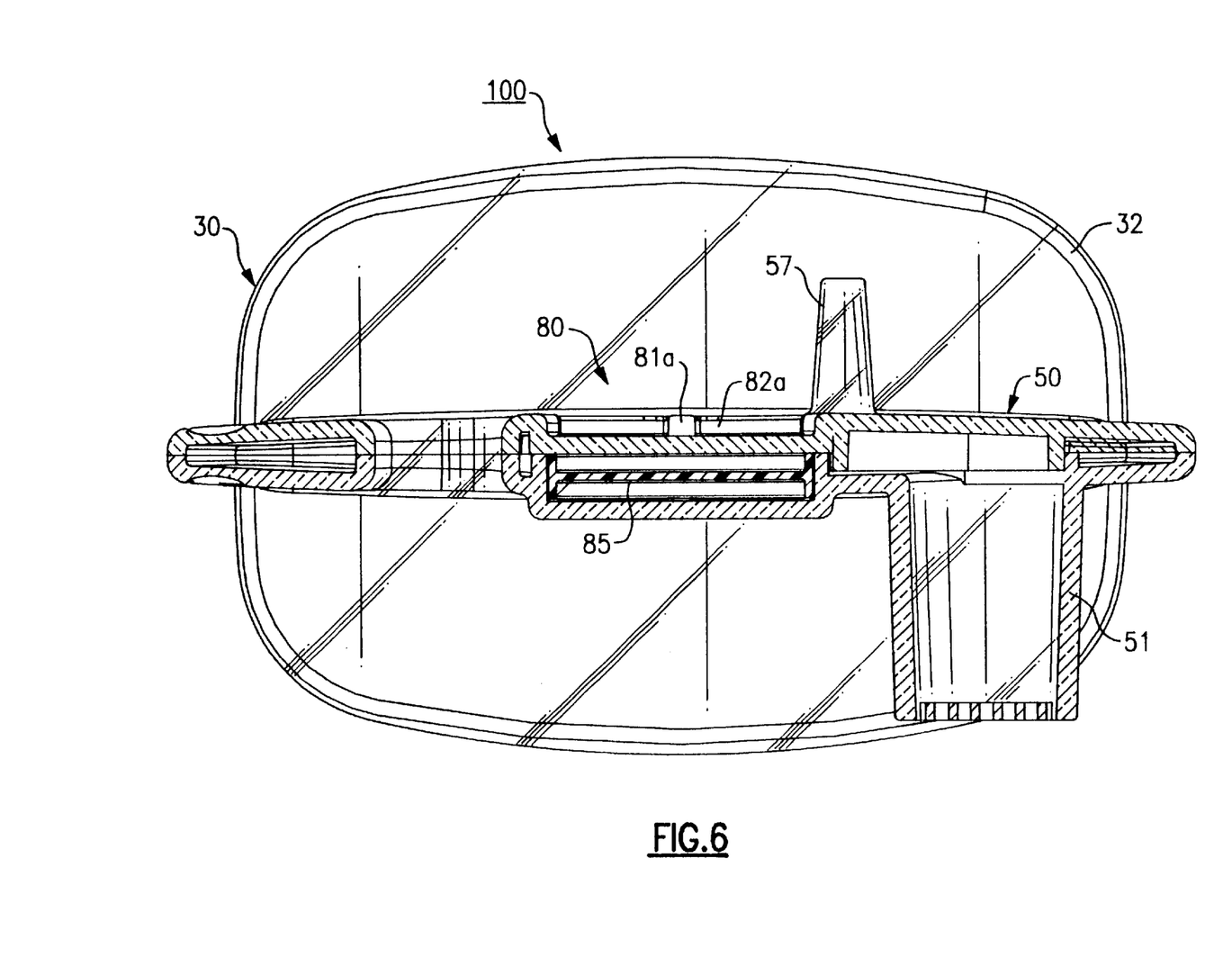
FIG. 6 is a cross-sectional view of the invention illustrated in FIG. 3 taken along line 6—6 to better illustrate the internal construction thereof.
Figure 7:
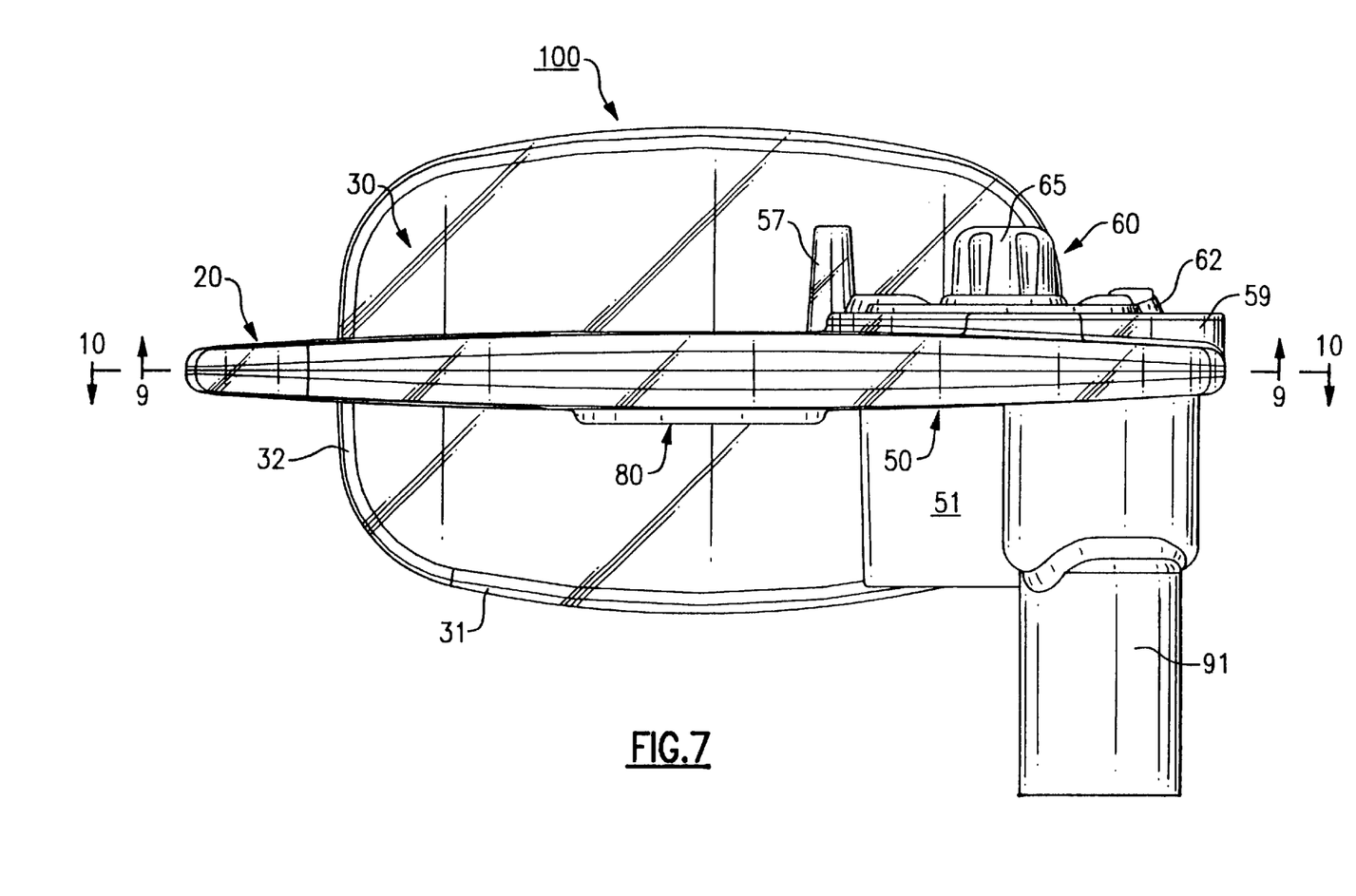
FIG. 7 is a top planar view of the invention illustrated in FIG. 3.

To meter the flow rate of the inspiratory air being inhaled by the patient, the back wall 54 carries a rotatable dial 60 formed with a plurality of air-flow-control openings 61 having different diameters to form inlet orifices through which a patient withdraws inspiratory air. As best illustrated in FIG. 5, rotation of the dial 60 selectively positions one of the plurality of air-flow-control openings 61 in alignment with an opening 55 in the back wall 54 to control the flow of inspiratory air which is thereby inhaled at a predetermined flow rate which is visually monitored by the patient in a manner to be hereinafter described below.

As best illustrated in FIGS. 3–6, 9 and 10, the spirometer 100 is sealed from the entry of ambient air except through an oxygen port 57, an indicator channel inlet or opening 82a formed in the bottom of an indicator channel 88, and the opening 55 in the back wall 54 through which inspiratory air is drawn into the spirometer 100 through the particular air-flow-control opening 61 which has been positioned over the aperture 55 formed in the back wall 54. In this manner, the flow rate of inspiratory air withdrawn from the spirometer 100 by a patient through the inspiratory air withdrawal port 51 maybe regulated by the air-flow-control opening 61 positioned over the aperture 55, in a manner to be hereinafter described in detail.

Figure 9:
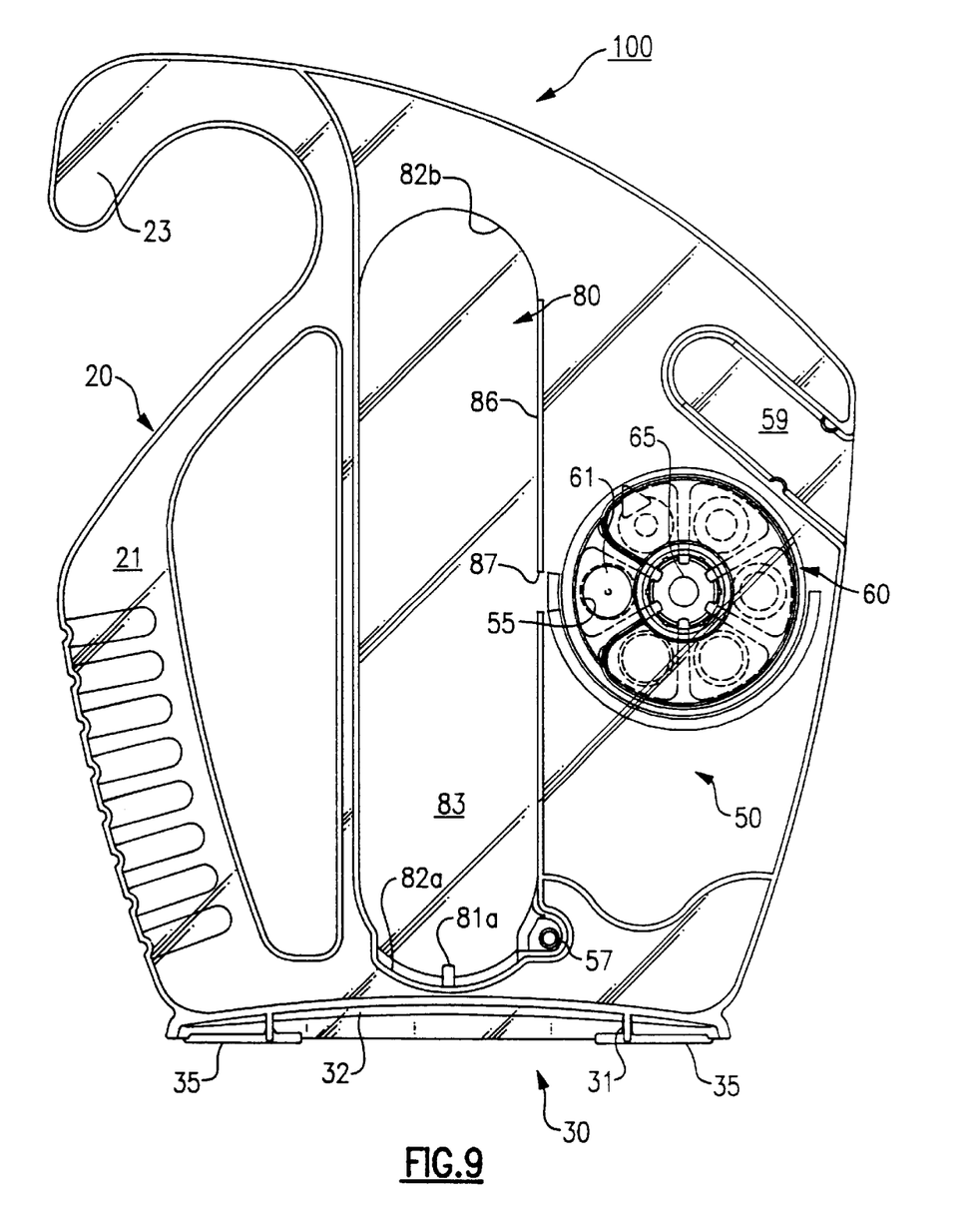
FIGS. 9 and 10 are cross-sectional views of the invention illustrated in FIG. 3 taken along lines 9—9 and 10—10, respectively, to better illustrate the manner in which air flows through the spirometer.
Figure 10:
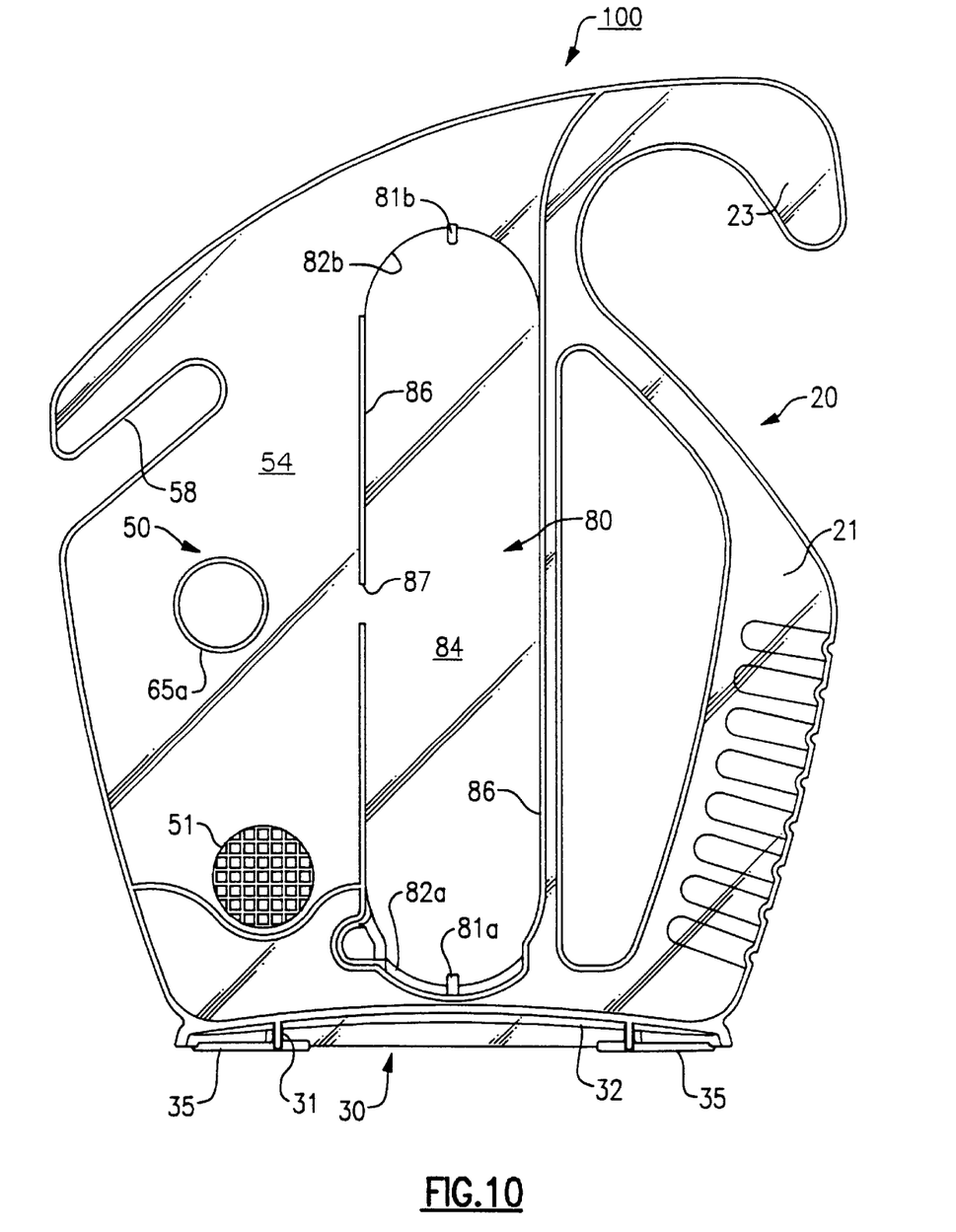

The oxygen inlet port 57, formed in the back wall 54 to communicate with the interior of the spirometer 100, is provided to connect a source of oxygen for administration to the patient. The oxygen inlet port 57 extends through the back wall 84 and terminates, as best shown in FIGS. 9 and 10, adjacent to the indicator channel air inlet opening 82a through which ambient air is drawn by the patient. In this manner the oxygen inlet port 57 is positioned such that the flow of oxygen is directed into the ambient inspiratory air when the patient inhales through the mouthpiece 91 so that when oxygen is being supplied through the oxygen inlet port 57 the flow of oxygen will not effect the flow rate of the patient created air flow applied to the spirometer 100 when in use. Oxygen discharged into the spirometer 100 through the oxygen inlet port 57 enters the indicator channel 88 through the inlet opening 82a, and is drawn upwardly with ambient air entering the indicator channel 88 through the inlet opening 82a when the patient inhales through the inspiratory air withdrawal port 51. Air, with or without supplemental oxygen, passes out from the indicator channel 88 through an indicator channel outlet opening 82b formed in the top of the indicator channel 88 to be withdrawn by the patient from the spirometer 100 through the inspiratory air withdrawal port 51. In this manner, the use of supplemental oxygen will not effect the monitoring of the inspiratory air flow rate through the monitoring portion 80 of the spirometer 100.

The Rotatable Dial 60

Figure 8:
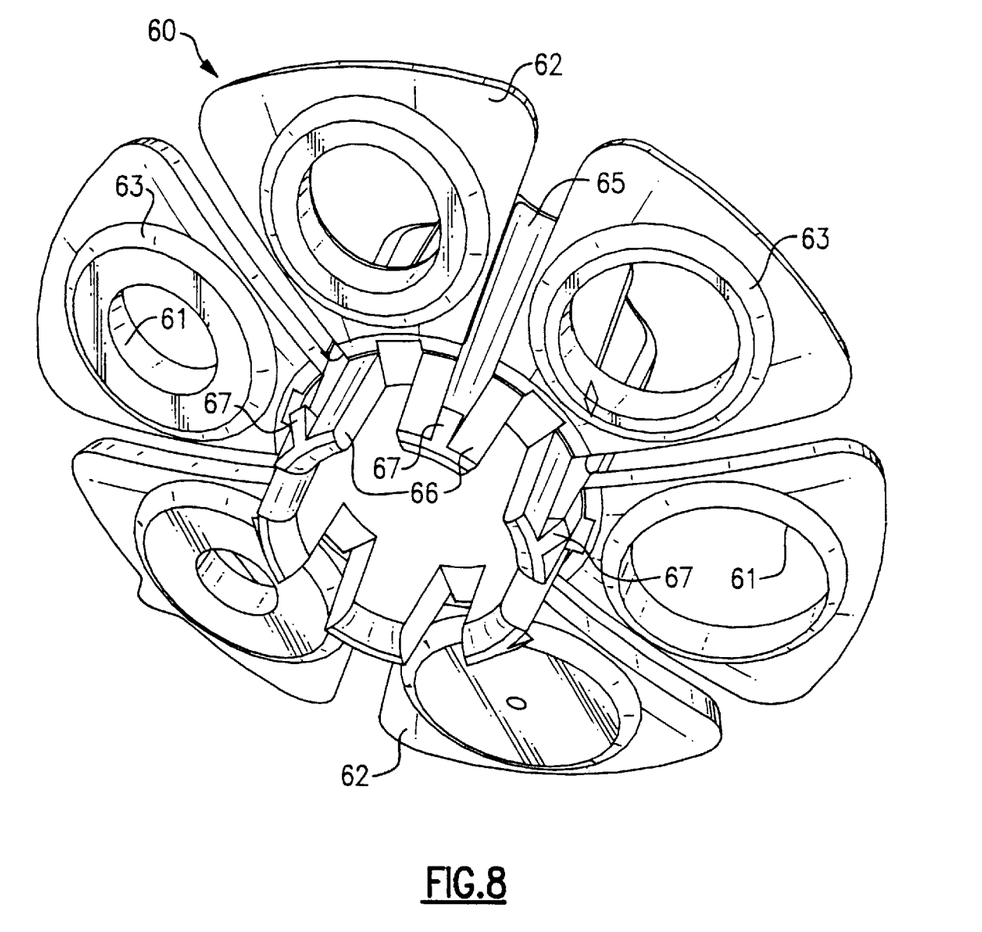
FIG. 8 is an enlarged perspective view of the dial used in the invention to regulate the air flow.

The structure of the rotatable dial 60, which controls the metering air flow into the flow rate determining portion 50, is best illustrated in FIG. 8. In the preferred embodiment of this invention the dial 60 is formed with six individual air-flow-control openings 61, each having a different sized orifice formed therein through which a patient draws a portion of the inspiratory air withdrawn into the spirometer 100. As illustrated in FIG. 5, the back wall 54 of the spirometer is formed with an opening 55 with which each one of the air-flow-control openings 61 may be selectively aligned by rotation of the dial 60. The face portion 56 of the back wall against which the dial 60 rotates is recessed in a cup shape to facilitate sealing the rotatable dial 60 against the back wall 54 to minimize or eliminate the flow of inspiratory air into the spirometer except through the particular air-flow-control opening 61 which is aligned with the opening 55 in the back wall 54.

To retain the rotatable dial 60 in proper position against the cup-shaped recessed face portion 56 the dial is formed with a hub portion 65, by which the dial is rotated, having a plurality of resilient tangs 66 extending outwardly therefrom. Each one of the resilient tangs 66 has a tapered shoulder stop 67 formed at the free end thereof. The dial 60 is mounted to the back wall 54 by inserting the tangs 66 through an opening 56a in the center of the cup-shaped recess 56 which is closed to the entry of ambient air into the spirometer. A cup-shaped cowling 65a is formed on the front wall 53 to receive the hub portion 65 when the hub portion 65 is inserted through the opening 56a on the back wall 54. The cup-shaped cowling 65a is then sealed against the back wall 54 to prevent leakage of ambient air into the spirometer through the opening 56a. The tangs 66 pass through the opening 56a, and the tapered shoulder stops 67 thereof press outwardly against a shoulder 56b to retain the rotatable dial 60 against the cup-shaped recess 56.

The individual air-flow-control openings 61 are each formed in individual petal-shaped flaps 62 which extend outwardly as cantilevers from the hub 65. The cantilever construction of the flaps 62 creates a loading force against the cup-shaped recess 56 when the dial 60 is installed into the opening 56a of the spirometer, to minimize or eliminate the passage of ambient air into the spirometer 100 except through one of the air-flow-control openings 61. To this same end, a tapered rim 63 extends about each of the air-flow-control openings 61 and is formed with an outer diameter of a size to sealingly engage with the opening 55 formed in the back wall 54 for minimizing or eliminating the passage of additional ambient air into the spirometer other than through one of the openings 61.

The Monitoring Portion 80

The monitoring portion 80 permits the patient to monitor the inspiratory air flow rate being applied by the patient's respiratory system during therapy and, in cooperation with the flow rate determining portion 50, insures that a patient is receiving the desired therapy. To this end, the monitoring portion 80 includes the "puck" shaped indicator 85 which has a predetermined weight, preferably approximately 1.114 grams, and which is vertically moveable in response to the patient induced air flow between two parallel guide rails 86 (best shown in FIGS. 3,9 and 10) formed between a front wall 83 and a back wall 84 of the monitoring portion 80 to define the indicator channel 88. The indicator channel 88 in which the puck or indicator 85 is vertically moveable in response to the flow rate of patient induced inspiratory air, is formed between the front and back walls 83, 84 and the guide rails 86. The channel 88 is in fluid communication with the inspiratory air port 51 so that as a patient draws inspiratory air through the mouthpiece 91 inspiratory air will be drawn through the indicator channel inlet opening 82a and the oxygen port 57 into the indicator channel 88 to draw the indicator puck 85 upwardly as the combined air flows pass out of the indicator channel 88 through the indicator channel outlet opening 82b formed at the top thereof.

To control the flow rate of inspiratory air being withdrawn by the patient through the inspiratory air withdrawal port 51, the air-flow through the metering aperture 87 formed in one of the parallel guide rails 86 functions to control the upward vertical movement of the indicator 85 as it is drawn upwardly in the channel 88. To this end a visual indicator 89, illustrated for example as a smiling face target and a pair of range defining arrowheads, is carried on the front wall 83 of the indicator channel 88 to provide a visual target for assisting the patient in maintaining the indicator puck 85 at the desired target position, the smiling face, which corresponds to a patients inhalation at the desired flow rate. To prevent the indicator puck 85 from being drawn upwardly to the top of the indicator channel 88, and thereby blocking the indicator channel discharge opening 82b, a stop 81b is formed at the upper portion of the indicator channel 88 to prevent the puck indicator 85 from closing the opening 82b. A similar stop 81a is formed at the bottom of the indicator channel 88 to hold the indicator puck 85 off of the indicator channel inlet opening 82a in the channel bottom which would inhibit entry of ambient air, and supplemental oxygen if utilized, to facilitate the raising of the indicator puck when inspiratory air is initially withdrawn by the patient.

Because the puck or indicator 85 is of a fixed size and a fixed weight, preferably about 1.114 grams, and the indicator channel 88 is a fixed cross-sectional dimension, an inspiratory air-flow rate entering the spirometer solely through the indicator channel inlet opening 82a can be determined which will be sufficient to cause the indicator puck 85 to be drawn upwardly in the indicator channel, thereby establishing a base air-flow rate. For convenience of manufacturing, it is preferable that this base air-flow rate be established when the rotatable dial 60 is set at the smallest opening. In this manner, the smallest opening can be varied from total occlusion to the flow of air, to an aperture of a size to accomplish the purpose of setting the base air-flow rate from which the size of the other apertures will be formed to provide stepped increments for increased inspiratory air-flow.

Once the base air-flow rate has been established, the introduction of an additional source of air-flow through an air-flow-control opening 61 of the rotatable dial 60 will require the patient to create an inspiratory air-flow rate in excess of the base air-flow rate in order to raise the puck 85 to a position where the puck will occlude, that is be positioned to hinder the flow of inspiratory air through the air-flow metering aperture 87. Preferably, the air-flow-control openings 61 are sized to increase the inspiratory air flow rate in uniform increments, such as 6 liters per minute (l/m). The puck shape of the indicator 85 creates a plus or minus air-flow differential, preferably +/−2 l/m, when the puck is positioned to occlude the flow of inspiratory air through the air-flow metering aperture 87. This air-flow differential corresponds to the range defining arrowheads marked on the front wall 83 of the indicator channel 88, with the smiley face portion of the visual target 89 corresponding to a desired flow-rate which will balance the indicator puck 85 for the particular air-flow-control opening 61 selected. Initially when a patient inhales air at a particular flow rate, and the puck-shaped indicator 85 is resting on the bottom stop 81a, inspiratory air will be drawn from the monitoring chamber 88 through the indicator channel outlet opening 82b and the metering orifice 87 causing the puck 85 to rise. As the puck 85 rises in response to the patient's inhaling, the puck 85 will occlude, or partially occlude, the air-flow metering aperture 87 through which inspiratory air is drawn out of the monitoring chamber 88 into the flow-rate determining portion 50 of the spirometer. When the air-flow metering aperture 87 is so occluded, the puck 85 will stop rising and remain blocking the air-flow metering aperture 87 at a position which corresponds to the position of the smiley face of the visual indicator 89. Because the indicator 85 is puck shaped, the puck may rise slightly above this blocking position and then "sink" back to the occluding position, or below, and then be drawn up again. This "floating" of the puck 85 relative to occluding the air flow through the air-flow metering aperture 87 has been found to generate the +/−2 l/m air-flow differential and is marked by the points of the arrow heads of the indicator 89.

When it is desired to increase the flow-rate at which a patient will inhale inspiratory air, the rotatable dial 60 is rotated until a larger air-flow-control orifice 61 is positioned adjacent to the opening 55. This will increase the air-flow rate required to be inhaled by the patient in order to "balance" the puck 85 at the smiley face portion of indicator 89. In this manner a patient can utilize the spirometer throughout a range of different intensity deep breathing exercises, and the spirometer also can be utilized by different patients having a range of different capabilities for inhaling inspiratory air.

The Base Portion 30

Figure 1:
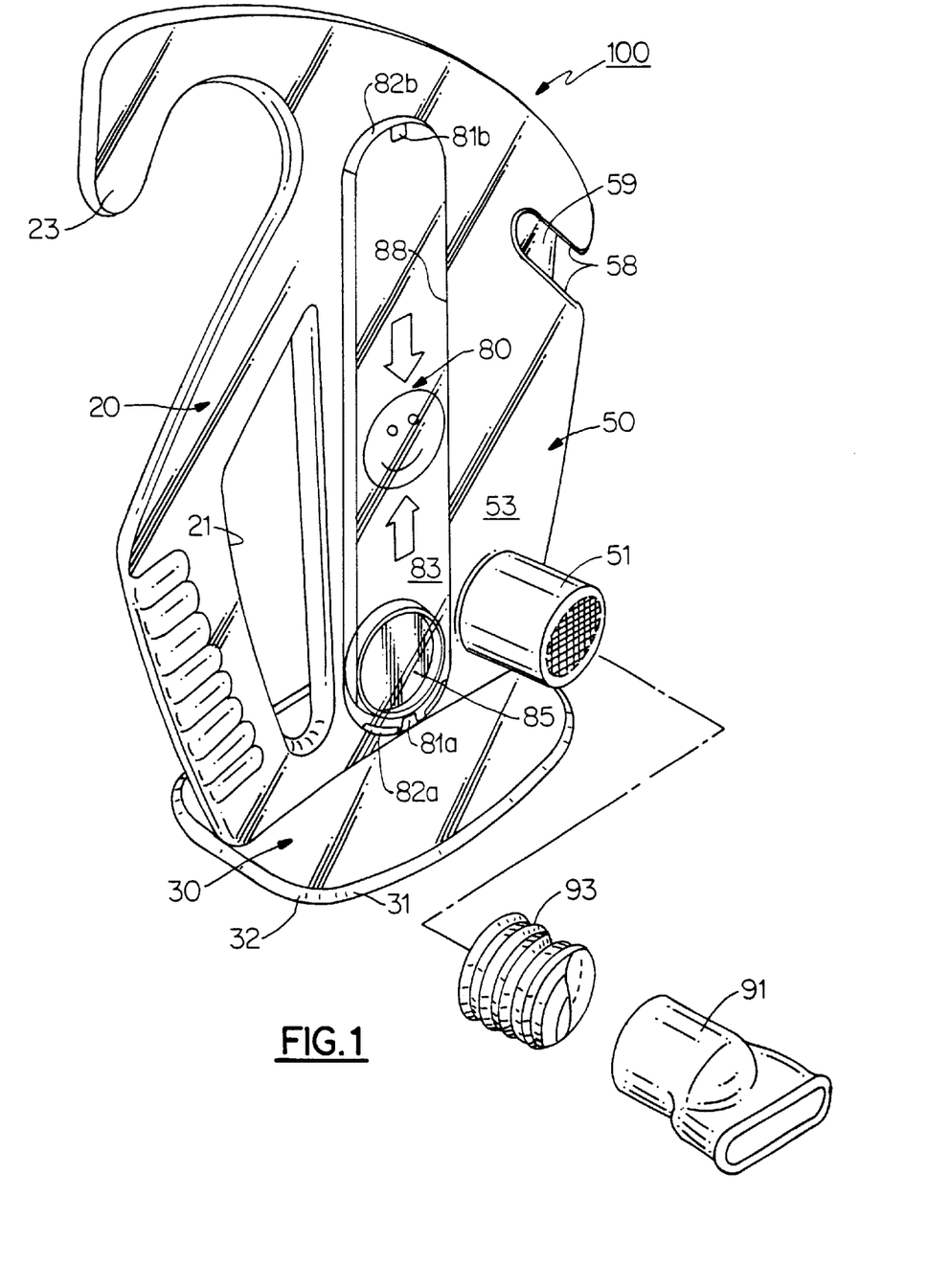
FIG. 1 is a frontal perspective view of the flow based incentive spirometer.
Figure 2:
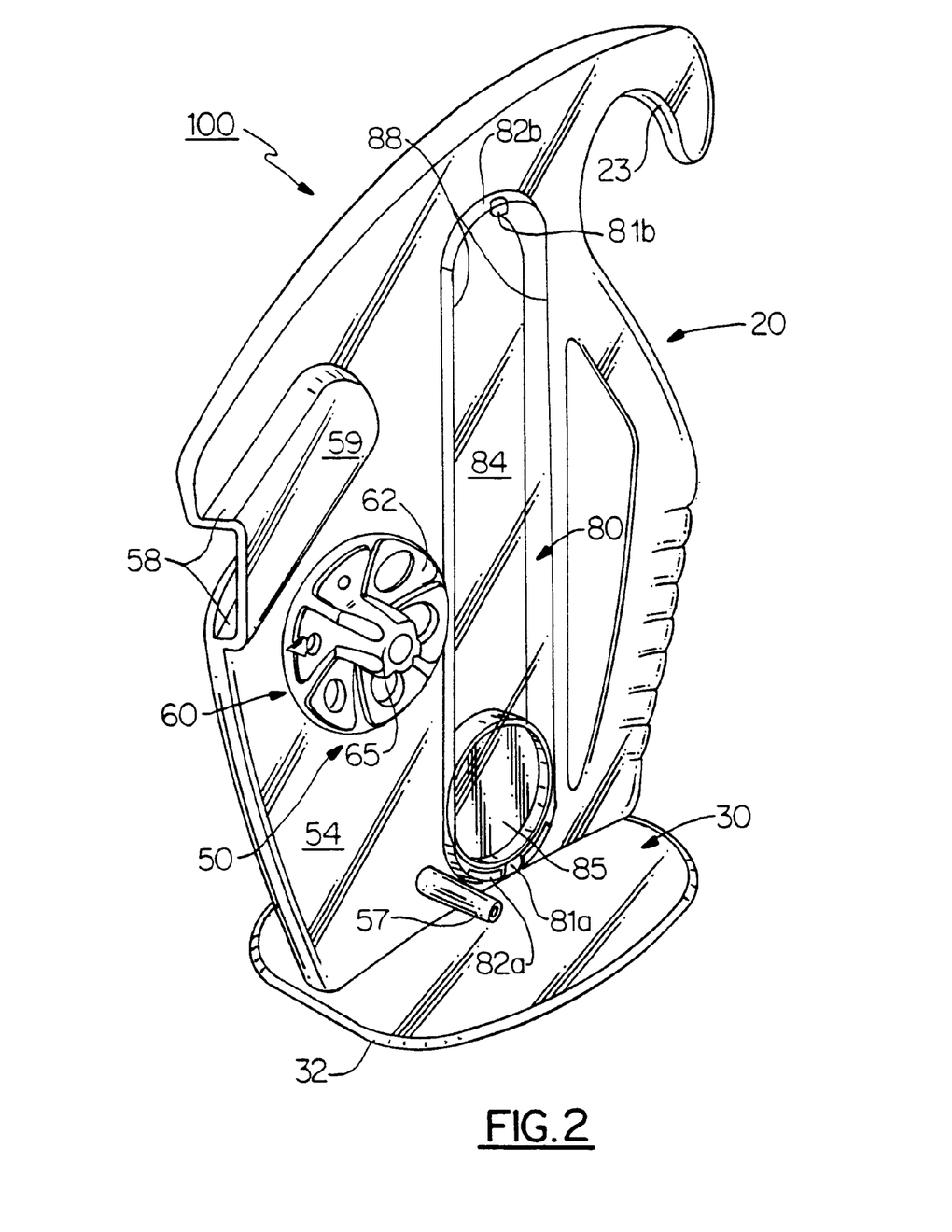
FIG. 2 is a rear perspective view of the flow based incentive spirometer of the present invention.
Figure 3:
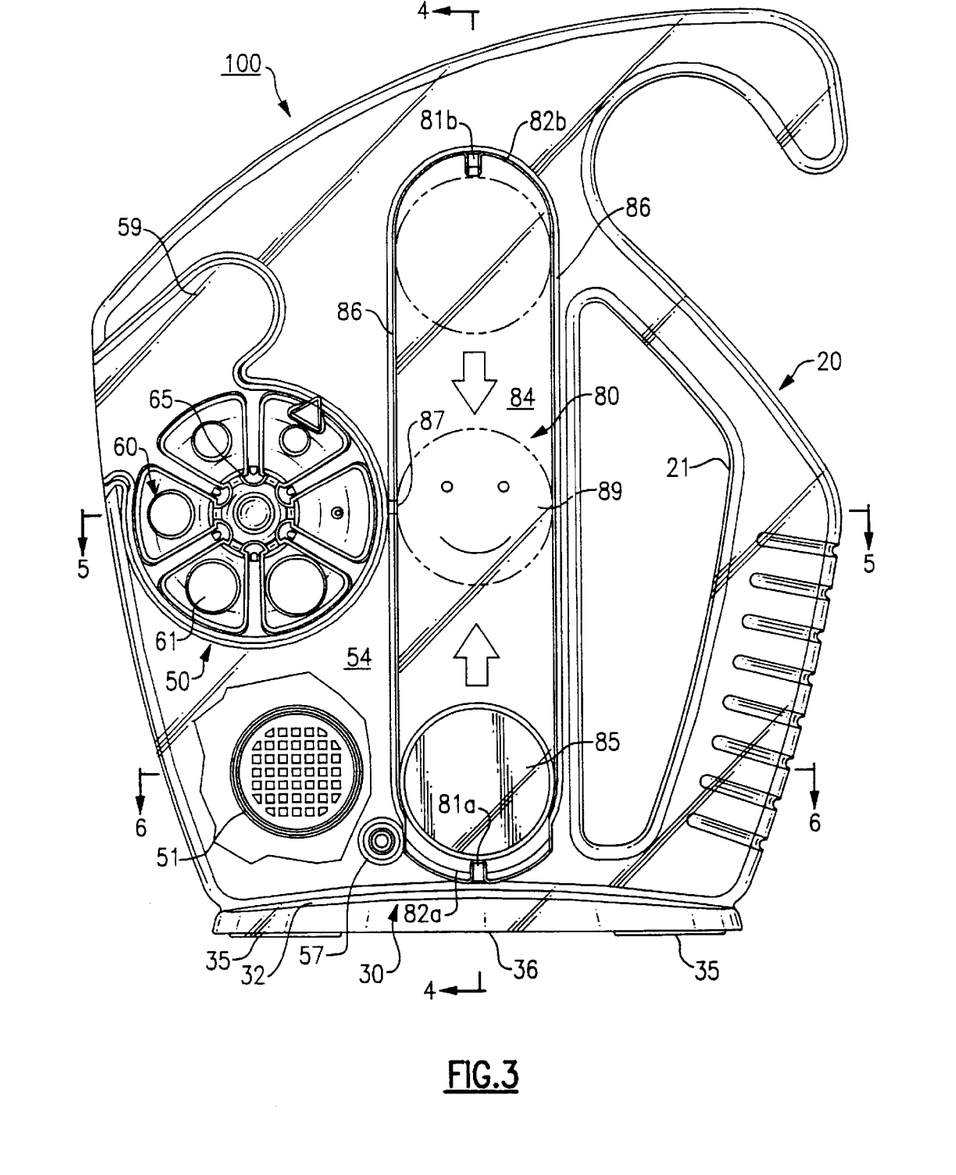
FIG. 3 is a rear elevational view of the invention with portions broken away to better illustrate the internal construction thereof.
Figure 4:
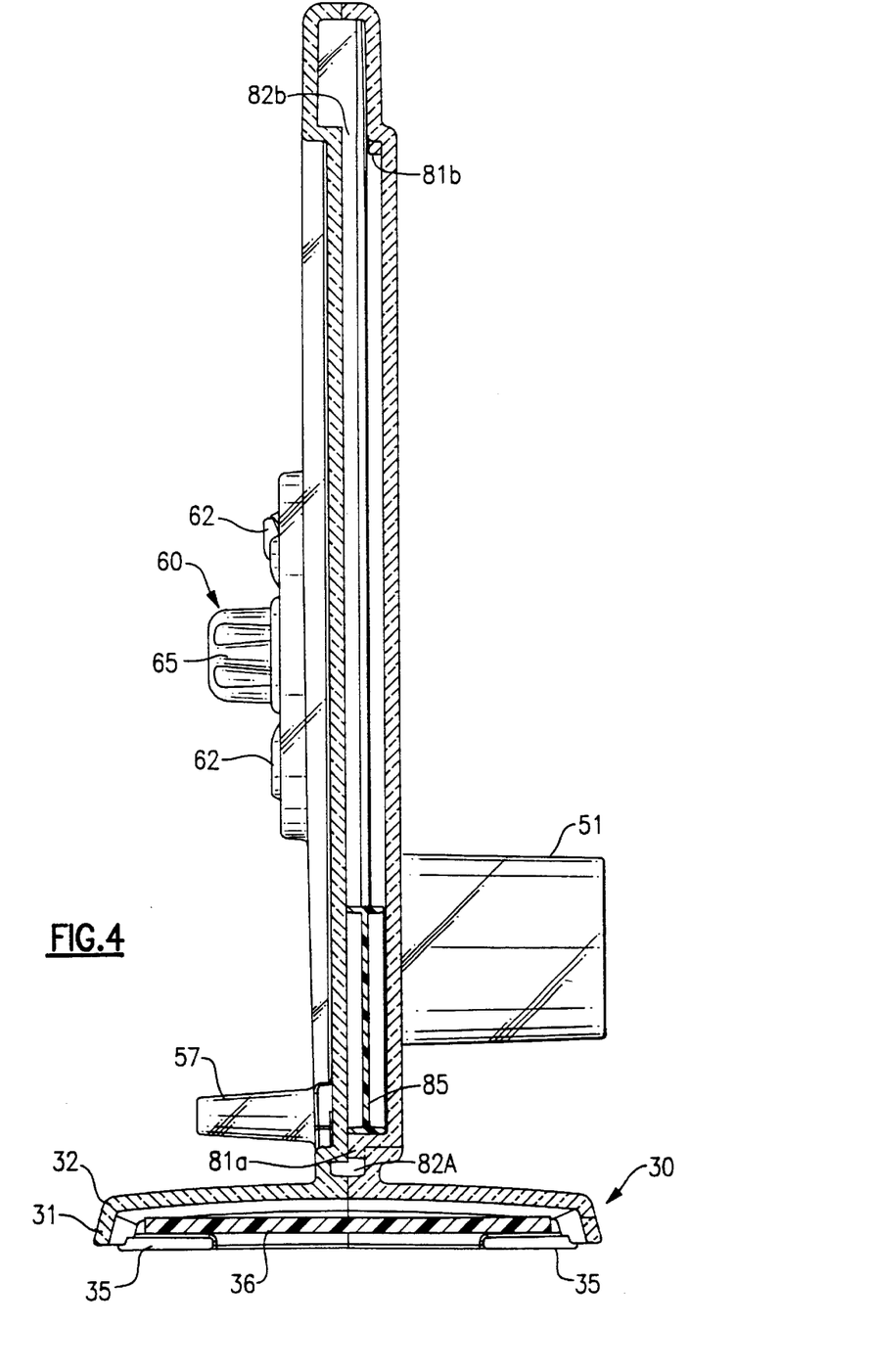
FIG. 4 is a cross-sectional view of the invention as illustrated in FIG. 3 taken along lines 4—4.

In order to permit the patient to conveniently observe the instructions for use of the device, and to maintain those instructions in an accessible fashion, the base portion 30 is formed of a transparent material with an opening 31 in a skirt portion 32 of the base, best illustrated in FIGS. 3 and 4. The opening 31 is formed between the top of the base and base pads 35 upon which the device stands. In this manner documentary materials, such as the instructions 36 for the use of the device, can be inserted into the base through the opening 31, and will be supported by the base pads 35 above the surface upon which the device is placed. Because the base is preferably formed of a transparent material, the instructions may be folded in a manner so that they are observable through the top and the bottom of the base to facilitate a patient's reference to them while the device is in use.

The Handle Portion 20

The handle portion 20 includes a closed portion forming a handle 21 enabling a patient to grasp and carry the spirometer 100 and an open hook projection 23 formed at the uppermost part of the handle portion 20 to enable the spirometer to be conveniently hung over a rail or a portion of a bed for convenient access by patients that are so confined.

While this invention has been described in the specification and illustrated in the drawings with reference to a preferred embodiment, the structure of which has been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

What is claimed is:

1. A flow based incentive spirometer through which a patient withdraws inspiratory air for receiving respiratory therapy, comprising:

an air flow rate chamber for setting an inspiratory air flow rate to permit a patient to inhale inspiratory air at a predetermined rate of air flow;

said air flow rate chamber including an inlet opening and an air-flow-metering aperture for controlling the rate of air flow therethrough, said air flow rate chamber further including a plurality of mutually exclusively patient positionable air-flowcontrol orifices of different sizes selectively positionable in fluid communication with said air-flow-metering aperture to control the rate of air flow therethrough;

a monitoring chamber in fluid communication with said air flow rate chamber to receive inspiratory air passed through said inlet opening in fluid communication therewith; and said monitoring chamber including an indicator responsive to the flow rate of inspiratory air passed from an outlet of said monitoring chamber and the air-flow-metering aperture into said air flow rate chamber to enable a patient to monitor the rate of flow of inspiratory air being drawn into the spirometer.

2. The flow based incentive spirometer of claim 1 further including an inlet for communicating a source of oxygen to said air flow rate chamber for mixing with the inspiratory air passing into said air flow rate chamber through said air flow rate chamber inlet opening.

3. The flow based incentive spirometer of claim 1 wherein said spirometer further includes a support base having a portion thereof which is transparent, and a plurality of support pads formed on said support base adjacent to said transparent portion for receiving display information visually observable to a patient through said transparent portion when self-administering respiratory therapy.

4. The flow based incentive spirometer of claim 1 further including a closed loop handle for carrying said spirometer and an open hook by which said spirometer may be hung.

5. The flow based incentive spirometer of claim 1 wherein said indicator responsive to the flow rate of inspiratory air received into said air flow rate chamber from said monitoring chamber comprises a puck of a predetermined weight moveable in response to the rate at which a patient inhales inspiratory air.

6. The flow based incentive spirometer of claim 5, further including indicia carried by said monitoring portion to facilitate the inhalation of inspiratory air at a desired rate of air flow.

7. The flow based incentive spirometer of claim 1 further including a retainer portion for receiving and retaining a mouthpiece for use by a patient when inhaling inspiratory air.

8. The flow based incentive spirometer of claim 7 wherein said retainer portion is formed as a recessed portion of a front wall of said spirometer and a complementary outwardly extending offset portion of a back wall of said spirometer.

9. The flow based incentive spirometer of claim 1 wherein the flow of inspiratory air through said inlet opening establishes an air-flow-rate base and the flow of inspiratory air through said air-flow rate chamber is variable in response to the positioning of one of said plurality of mutually exclusively positionable air-flow-control orifices of different sizes selectively positionable in fluid communication with said air-flow rate chamber.

10. A flow based incentive spirometer through which a patient withdraws inspiratory air for receiving respiratory therapy comprising:

an air flow rate chamber for setting an inspiratory air flow rate to permit a patient to inhale inspiratory air at a predetermined rate of air flow;

said air flow rate chamber including an inlet opening and an air-flow-metering aperture for controlling the rate of air flow therethrough, said air flow rate chamber further including a plurality of mutually exclusively positionable air-flow-control orifices of different sizes selectively positionable in fluid communication with said air-flow-metering aperture to control the rate of air flow therethrough;

said plurality of mutually exclusively positionable air-flow-control orifices of different sizes selectively positionable in fluid communication with said air-flow-metering aperture to control the rate of air flow therethrough being carried on a rotatable hub, a monitoring chamber in fluid communication with said air flow rate chamber to receive inspiratory air passed through said inlet opening in fluid communication therewith; and said monitoring chamber including an indicator responsive to the flow rate of inspiratory air passed from an outlet of said monitoring chamber and the air-flow-metering aperture into said air flow rate chamber to enable a patient to monitor the rate of flow of inspiratory air being drawn into the spirometer.

11. The flow based incentive spirometer of claim 10 wherein at least one of said air-flow-control orifices includes a tapered rim portion encircling said orifice to facilitate a seal between said air-flow-control orifice and said air flow rate chamber.

12. The flow based incentive spirometer of claim 11, wherein said air-flow-control orifices are carried on a petal-shaped flap cantilever connected to said rotatable hub.

13. A method for post-surgical prevention and treatment of atelectasis, and for sustained maximal inspiration exercise comprising the steps of:

inhaling inspiratory air from an inspiratory air withdrawal port of a flow based spirometer;

introducing said inspiratory air into said flow based spirometer through an air flow monitoring chamber in said flow based spirometer having an inlet opening in a bottom portion of said air flow monitoring chamber;

said air flow monitoring chamber including an air flow indicator movable within said air flow monitoring chamber in response to the flow of inspiratory air out from said air flow monitoring chamber and through said inspiratory air withdrawal port;

dividing said air flow of inspiratory air passing out from said air flow monitoring chamber into a first air flow path extending from said inlet opening in a bottom portion of said air flow monitoring chamber through an upper discharge opening of said air flow monitoring chamber and through said inspiratory air withdrawal port, and into a second air flow path extending from said inlet opening in a bottom portion of said air flow monitoring chamber through a patient operable adjustable air flow metering aperture formed in said air flow monitoring chamber at a location removed from and below said upper discharge opening and through said inspiratory air withdrawal port; and varying the flow of air from said air flow monitoring chamber in said second air flow path extending from said inlet opening in a bottom portion or said air flow monitoring chamber through said air flow metering aperture in response to said air flow indicator movable within said air flow monitoring chamber.

14. The method of claim 13 including the step of controlling the flow rate of inspiratory air from said inspiratory air withdrawal port by varying the flow rate of inspiratory air passing out from said air flow monitoring chamber through said second air flow path.

15. The method of claim 14 wherein said flow rate of inspiratory air passing out from said air flow monitoring chamber through said second air flow path is selectively varied to vary the flow rate of inspiratory air inhaled from said inspiratory withdrawal port.

* * * * *

UNITED STATES PATENT AND TRADEMARK OFFICE
CERTIFICATE OF CORRECTION

PATENT NO. : 6,656,129 B2
DATED : December 2, 2003
INVENTOR(S) : Niles et al.

It is certified that error appears in the above-identified patent and that said Letters Patent is hereby corrected as shown below:

<u>Title page,</u>
Item [73], Assignees, remove the "s" from "Assignees" and delete all four names listed after "Assignees", and replace with -- DHD Healthcare Corporation --.

Signed and Sealed this

Twenty-fifth Day of October, 2005

JON W. DUDAS
*Director of the United States Patent and Trademark Office*